(12) United States Patent
Bearman et al.

(10) Patent No.: US 6,403,332 B1
(45) Date of Patent: Jun. 11, 2002

(54) SYSTEM AND METHOD FOR MONITORING CELLULAR ACTIVITY (75) Inventors: Gregory H. Bearman, Pasadena; Scott E. Fraser, LaCanada-Flintridge; Russell D. Lansford, Claremont, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/628,219

(22) Filed: Jul. 28, 2000

Related U.S. Application Data (60) Provisional application No. 60/146,490, filed on Jul. 30, 1999, and provisional application No. 60/164,504, filed on Nov. 9, 1999.

(51) Int. Cl.[7] .............................. C12Q 1/02; C12Q 1/00
(52) U.S. Cl. .............................. 435/29; 435/4; 435/968; 435/283.1; 435/287.1; 435/288.7
(58) Field of Search .................... 435/29, 4, 968, 435/283.1, 287.1, 288.7

(56) References Cited

U.S. PATENT DOCUMENTS

| | | | |
|---|---|---|---|
| 4,844,617 A | 7/1989 | Kelderman et al. | 356/372 |
| 4,852,955 A | 8/1989 | Doyle et al. | 350/1.2 |
| 4,905,169 A | 2/1990 | Buican et al. | 364/525 |
| 5,011,243 A | 4/1991 | Doyle et al. | 350/1.2 |
| 5,034,613 A | 7/1991 | Denk et al. | 250/458.1 |
| 5,091,652 A | 2/1992 | Mathies et al. | 250/458.1 |
| 5,117,466 A | 5/1992 | Buican et al. | 382/6 |
| 5,192,980 A | 3/1993 | Dixon et al. | 356/326 |
| 5,239,409 A | 8/1993 | Doyle et al. | 359/351 |
| 5,329,352 A | 7/1994 | Jacobsen | 356/301 |
| 5,377,003 A | 12/1994 | Lewis et al. | 356/300 |
| 5,418,371 A | 5/1995 | Aslund et al. | 250/458.1 |
| 5,504,336 A | 4/1996 | Noguchi | 250/458.1 |
| 5,510,894 A | 4/1996 | Batchelder et al. | 356/301 |
| 5,532,873 A | 7/1996 | Dixon | 359/388 |
| 5,539,517 A | 7/1996 | Cabib et al. | 356/456 |
| 5,583,342 A | 12/1996 | Ichie | 250/459.1 |
| 5,612,818 A | 3/1997 | Kumagai et al. | 359/385 |

(List continued on next page.)

FOREIGN PATENT DOCUMENTS

| | | | |
|---|---|---|---|
| EP | 0 916 981 | 5/1999 | G02B/21/00 |
| WO | 96/22521 | 7/1996 | G01N/21/64 |
| WO | 99/37999 | 7/1999 | G01N/21/64 |
| WO | WO 01/09592 | 2/2001 | |

OTHER PUBLICATIONS

Bacallao, Robert, et al., "Guiding Principles of Specimen Preservation for Confocal Fluorescence Microscopy", Handbook of Biological Confocal Microscopy, Chapter 18, pp. 197–205, Plenum Press, United States of America.

Bacallao, Robert, et al., "Three–Dimensional Confocal Microscopy: Volume Investigation of Biological Specimens", 3D vol. Reconstruction, 1994, pp. 172–174, Academic Press.

Boardman, Joe W., "Inversion of Imaging Spectrometery Data Using Singular Value Decomposition", IGARSS'89 12th Canadian Symposium on Remote Sensing, Remote Sensing: An Economic Tool for the Nineties, Jul. 1989, pp. 2069–2072, vol. 4, IEEE, Canada.

(List continued on next page.)

*Primary Examiner*—Louise N. Leary
(74) *Attorney, Agent, or Firm*—Christie, Parker & Hale, LLP (57) ABSTRACT

A system and method for monitoring cellular activity in a cellular specimen. According to one embodiment, a plurality of excitable markers are applied to the specimen. A multiphoton laser microscope is provided to excite a region of the specimen and cause fluorescence to be radiated from the region. The radiating fluorescence is processed by a spectral analyzer to separate the fluorescence into respective wavelength bands. The respective bands of fluorescence are then collected by an array of detectors, with each detector receiving a corresponding one of the wavelength bands.

33 Claims, 7 Drawing Sheets

U.S. PATENT DOCUMENTS

| | | | |
|---|---|---|---|
| 5,658,423 A | 8/1997 | Angell et al. | 438/9 |
| 5,674,743 A | 10/1997 | Ulmer | 435/287.2 |
| 5,713,364 A | 2/1998 | DeBaryshe et al. | 128/664 |
| 5,719,391 A | 2/1998 | Kain | 250/235 |
| 5,732,150 A | 3/1998 | Zhou et al. | 382/133 |
| 5,751,417 A | 5/1998 | Uhl | 356/318 |
| 5,754,296 A | 5/1998 | Law | 356/369 |
| 5,777,732 A | 7/1998 | Hanninen et al. | 356/318 |
| 5,784,162 A | 7/1998 | Cabib et al. | 356/346 |
| 5,785,651 A | 7/1998 | Kuhn et al. | 600/310 |
| 5,796,112 A | 8/1998 | Ichie | 250/458.1 |
| 5,804,813 A | 9/1998 | Wang et al. | 250/201.3 |
| 5,813,987 A | 9/1998 | Modell et al. | 600/473 |
| 5,814,820 A | 9/1998 | Dong et al. | 250/458.1 |
| 5,815,262 A | 9/1998 | Schrof et al. | 356/318 |
| 5,822,061 A | 10/1998 | Dalhaye et al. | 356/326 |
| 5,864,139 A | 1/1999 | Reffner et al. | 250/339.07 |
| 5,891,738 A | 4/1999 | Soini et al. | 436/501 |
| 6,077,665 A * | 6/2000 | Weirich et al. | 435/6 |

OTHER PUBLICATIONS

Boardman, Joseph W., et al., "Automated Spectral Analysis: A Geological Example Using Aviris Data, North Grapevine Mountains, Nevada", Presented at the Tenth Thematic Conference on Geologic Remote Sensing, May 1994, I–407 –I–418, United States of America.

Bock, G., et al., "Photometric Analysis of Antifading Reagents for Immunofluorescence with Laser and Conventional Illumination Sources", The Journal of Histochemistry and Cytochemistry, 1985, pp. 699–705, vol. 33, No. 7, The Histochemical Society, Inc., United States of America.

Castleman, Kenneth R., "Color compensation for digitized FISH Images", Bioimaging 1, 1993, pp. 159–165, IOP Publishing Ltd., United Kingdom.

Chen, Raymond F., et al., "Atlas of Fluorescence Spectra and Lifetimes of Dyes Attached to Protein", Analytical Letters, 1985, pp. 393–421, (18A4), Marcel Dekker, Inc.

Faust, Jessica A., et al., "Development of a Compact Imaging Spectrometer Using Liquid Crystal Tunable Filter Technology", IS&T/OSA Optics & Imaging in the Information Age, Oct. 20–24, 1996, pp. 429–432, IS&T–The Society for Imaging Science and Technology, United States of America.

Florijn, R. J., et al., "Analysis of Antifading Reagents for Fluorescence Microscopy", Cytometry, 1995, pp. 177–182, vol. 19, Wiley–Liss, Inc.

Green, Andrew A., et al., "A Transformation for Ordering Multispectral Data in Terms of Image Quality with Implications for Noise Removal", IEEE Transactions on Geoscience and Remote Sensing, Jan. 1988, pp. 65–74, vol. 26 No. 1 IEEE.

Green, Robert O., et al., "Imaging Spectroscopy and the Airborne Visible/Infrared Imaging Spectrometer (AVIRIS)", Remote Sens, Environ., Jul. 1998, pp. 227–248, vol. 65, Elsevier Science Inc., United States of America.

Heim, Roger, et al, "Engineering Green Fluorescent Protein for Improved Brightness, Longer Wavelengths and Fluorescence Resonance Energy Transfer", Current Biology, 1996, pp. 178–182, vol. 6, No. 2, Current Biology Ltd, United States of America.

Johnson, G. D., et al., A Simple Method of Reducing the Fading of Immunofluorescence during Microscopy, Journal of Immunological Methods, 1981, pp. 349–350, vol. 43, Elsevier/North–Holland Biomedical Press.

Johnson, G. D., et al., "Fading of Immunofluorescence during Microscopy: a Study of the Phenomenon and its Remedy", Journal of Immunological Methods, 1982, pp. 231–242, vol. 55, Elsevier Biomedical Press.

Kaufman, Arie., "Volume Visualization", 1991, IEEE Computer Society Press, pp. 1–18, United States of America.

Kinsella, Todd M., et al., "Episomal Vectors Rapidly and Stably Produce High–Titer Recombinant Retrovirus", Human Gene Therapy, Aug. 1996, pp. 1405–1413, vol. 7, Mary Ann Liebert, Inc.

Krenik, Karen D., et al., "Comparison of antifading agents used in immunofluorescence", Journal of Immunological Methods, 1989, pp. 91–97, vol. 117, Elsevier.

Leica, "Leica TCS MP Two Photo Imaging System", Confocal Spectrum, 1998, pp. 6, Lecia Micorsystems Heidelberg GmbH.

Longin, Arlette, et al., "Comparison of Antifading Agents Used in Fluorescence Microscopy: Image Analysis and Laser Confocal Microscopy Study", The Journal of Histochemistry and Cytochemistry, 1993, pp. 1833–1840, vol. 41, No. 12, The Histochemical Society, Inc, United States of America.

Lybarger, Lonnie, et al., "Dual–Color Flow Cytometric Detection of Fluorescent Proteins Using Single–Laser (488–nm) Excitation", Cytometry, 1998, pp. 147–152, vol. 31, Wiley–Liss, Inc., United States of America..

Morris, Hannah R., et al, "Imaging Spectrometers for Fluorescence and Raman Microscopy: Acousto–Optic and Liquid Crystal Tunable Filters", Applied Spectroscopy, Nov. 1994, pp. 857–866, vol. 48, United States of America.

Morrison, Larry, "CT 108, Spectral Overlap Corrections In Fluorescence in Situ Hybridizations Employing High Fluorophore Densities", Cytometry, 1998, p. 140, Suppl. 9, United States of America.

Pepperkok, Rainer, et al., "Simultaneous detection of multiple green fluorescent proteins in live cells by fluorescence lifetime imaging microscopy", Current Biology, 1999, 269–272, vol. 9, Elsevier Science Ltd.

Potter, Steve M., et al., "Neural Transplant Staining with DiI and Vital Imaging by 2–Photon Laser–Scanning Microscopy", Scanning Microscopy Supplement 10, 1996, 189–199, Scanning Microscopy International, United States of America.

Richards, John A., "Remote Sensing Digital Imaging Analysis", pp. 75–88, Springer–Verlag Berlin Heidelberg, Germany.

Stevens, John K., "Three–Dimensional Confocal Microscopy: Volume Investigation of Biological Specimens", 1994, pp. 8–13, Academic Press.

Tsien, Roger Y., et al., "Fluorophores for Confocal Microscopy: Photophysics and Photochemistry", Handbook of Biological Confocal Microscopy, 1990, pp. 169–178, Plenum Press, United States of America.

Wells, Sam, et al., "Fluorescent Labels for Confocal Microscopy", Three–Dimensional Confocal Microscopy: Volume Investigation of Biological Specimens, 1994, pp. 101–129, American Press, Inc.

* cited by examiner

SYSTEM AND METHOD FOR MONITORING CELLULAR ACTIVITY

CROSS-REFERENCE TO RELATED APPLICATIONS

This application is based on provisional patent application No. 60/146,490 filed Jul. 30, 1999, and No. 60/164,504 filed Nov. 9, 1999.

STATEMENT REGARDING FEDERALLY SPONSORED RESEARCH OR DEVELOPMENT

The invention described herein was made in the performance of work under a NASA contract, and is subject to the provisions of Public Law 96-517 (35 USC 202) in which the Contractor has elected to retain title.

FIELD OF THE INVENTION

The present invention relates to the monitoring of cellular activity through the use of excitable markers. More particularly, the invention relates to a system and method for using a plurality of fluorescent probes to monitor cellular activity.

BACKGROUND OF THE INVENTION

Presently, fluorescence microscopy is one of the most widely used microscopy techniques, as it enables the molecular composition of the structures being observed to be identified through the use of fluorescently-labeled probes of high chemical specificity, such as antibodies. However, its use is mainly confined to studies of fixed specimens because of the difficulties of introducing antibody complexes into living specimens. For proteins that can be extracted and purified in reasonable abundance, these difficulties can be circumvented by directly conjugating a fluorophore to a protein and introducing this back into a cell. It is believed that the fluorescent analogue behaves like the native protein and can therefore serve to reveal the distribution and behavior of this protein in the cell.

An exciting, new development in the use of fluorescent probes for biological studies has been the development of the use of naturally fluorescent proteins as fluorescent probes, such as green fluorescent protein (GFP). The gene for this protein has been cloned and can be transfected into other organisms. This can provide a very powerful tool for localizing regions in which a particular gene is expressed in an organism, or in identifying the location of a particular protein. The beauty of the GFP technique is that living, unstained samples can be observed. There are presently several variants of GFP which provide spectrally distinct emission colors.

Conventionally, fluorescence microscopy only worked well with very thin specimens or when a thick specimen was cut into sections, because structures above and below the plane of focus gave rise to interference in the form of out-of-focus flare. However, this can be overcome by optical sectioning techniques, such as multi-photon fluorescence microscopy.

Multi-photon fluorescence microscopy involves the illumination of a sample with a wavelength around twice the wavelength of the absorption peak of the fluorophore being used. For example, in the case of fluorescein which has an absorption peak around 500 nm, 900 nm excitation could be used. Essentially no excitation of the fluorophore will occur at this wavelength. However, if a high peak-power, pulsed laser is used (so that the mean power levels are moderate and do not damage the specimen), two-photon events will occur at the point of focus. At this point the photon density is sufficiently high that two photons can be absorbed by the fluorophore essentially simultaneously. This is equivalent to a single photon with an energy equal to the sum of the two that are absorbed. In this way, fluorophore excitation will only occur at the point of focus (where it is needed) thereby eliminating excitation of the out-of-focus fluorophore and achieving optical sectioning.

Often, multiple fluorophores are used, with each fluorophore having a different spectra, some of which may overlap. Typically, the ability to distinguish between the respective fluorophores is only possible where the excitation and emission spectra are separated, or where the fluorescence lifetimes are distinct.

Another approach is to selectively excite different fluorophores by using various excitation photon wavelengths, each of which will approximate the wavelength of the absorption peak of a corresponding fluorophore. Such an approach is not practical for a number of reasons. Firstly, it is difficult to rapidly tune the excitation wavelength of the laser providing the excitation photons. Secondly, there is typically a very broad excitation spectrum, so that such an approach makes it difficult to excite a single dye.

Thus, the need exists for a system and method for efficiently monitoring a plurality of fluorescent probes, and to selectively record the signal from those probes for subsequent analysis. The present invention addresses these needs.

SUMMARY OF THE INVENTION

Briefly, the present invention is directed to a system and method for monitoring cellular activity in a cellular specimen. According to one illustrative embodiment of the invention, a plurality of excitable markers are applied to the specimen. A multi-photon laser microscope is provided to excite a region of the specimen and cause fluorescence to be radiated from the region. The radiating fluorescence is processed by a spectral analyzer to separate the fluorescence into wavelength bands. The respective fluorescence bands are then collected by an array of detectors, with each detector receiving a corresponding one of the wavelength bands.

According to another embodiment, the invention is directed to a system for monitoring cellular activity in a cellular specimen that contains a plurality of excitable markers. The system includes a laser microscope that is operative to excite the markers in a region of the specimen, so that those markers in the region radiate fluorescence. The system also includes a tunable filter that is operative to process the fluorescence and to pass a portion of the fluorescence wavelengths radiated by the markers. The system still further includes a detector that is operative to receive the processed fluorescence wavelengths.

In still another embodiment, the invention is directed to a system for monitoring cellular activity, including a two-photon laser microscope that is operative to excite the markers in a region of the specimen such that the markers in the region radiate fluorescence. The system also includes a detector that is operative to receive non-descanned fluorescence from the specimen.

DETAILED DESCRIPTION OF THE INVENTION

Figure 1:
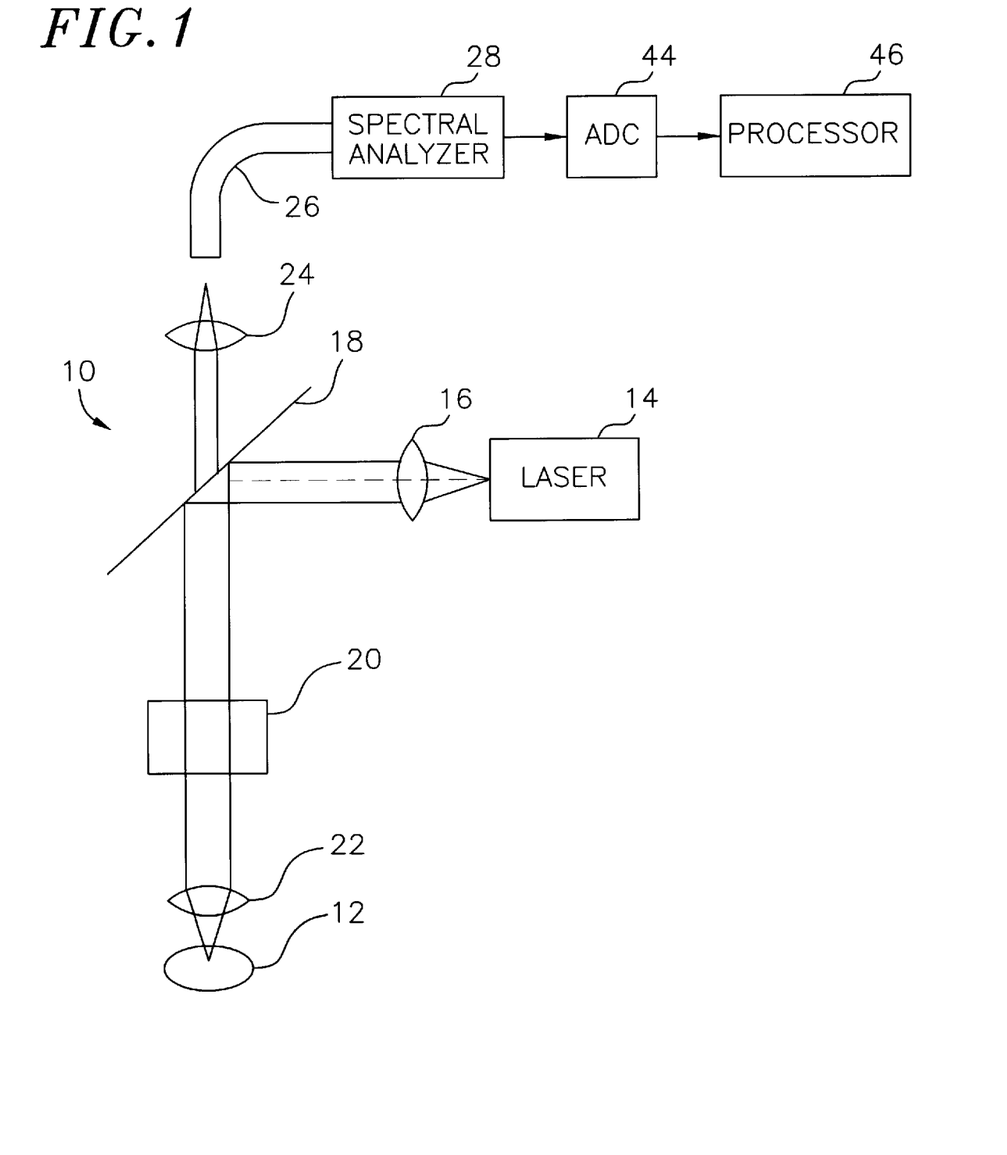
FIG. 1 is a schematic diagram of a first illustrative embodiment of the present invention.

Referring to FIG. 1, a novel system 10 is disclosed for capturing spectral data from a specimen 12 to which a plurality of excitable markers have been applied. In one embodiment, at least two fluorescent dyes (i.e., fluorescent probes) are applied to the specimen. The fluorescent dyes have respective emission spectra that may or may not overlap. In the case where the emission spectra are very similar, it becomes difficult to separate out the emission spectra to determine the contributions of each of the fluorescent dyes to the observed spectra. System 10 facilitates making such determinations in an efficient, reliable manner.

As shown in FIG. 1, system 10 includes a laser 14 that generates laser light. The light emitted by laser 14 is focused by a lens 16 onto a short pass dichroic mirror 18. As is well known, the dichroic mirror 18 selectively reflects light according to its wavelength. Thus, the dichroic mirror is selected such that it reflects the light emitted by laser 14.

The reflected light from dichroic mirror 18 is directed toward scanning optics, shown schematically at 20. The scanning optics may include a controllable deflection unit, or any other suitable structure that allows the reflected light to be redirected for scanning of the specimen 12 by the laser light, as is well known to those skilled in the art.

The directed light from scanning optics 20 is imaged by a microscope lens 22 onto or into the specimen 12. The laser light excites the fluorescent dyes in the region where the light is directed, such that those dyes fluoresce and emit light having respective emissions spectra.

In one embodiment, laser 14 is a two-photon laser. As is well known, a two-photon laser microscope depends on the two-photon effect, by which the fluorescent dyes are excited not by a single photon, but rather by two relatively low energy photons that are absorbed contemporaneously by a fluorescent dye. Thus, the requirement for two coincident (or near coincident) photons to achieve excitation of the fluorescent dye means that only focused light reaches the required intensities and that scattered light does not cause excitation of the fluorescent dyes. As such, a two-photon laser microscope is inherently insensitive to the effects of light scattering in thick slices. Alternatively, the laser 14 may comprise some other multi-photon laser, or a single-photon laser.

The fluoresence radiated by the excited dyes is focused by the microscope lens 22, and passes through the scanning optics 20 and dichroic mirror 18. The fluorescence is then focused by a lens 24 and directed to a light guide 26 that delivers the focused light to a spectral analyzer 28. Spectral analyzer 28 receives the light and disperses the light into respective wavelength bands. Each band is detected by a corresponding detector, and the intensity of each band is recorded and processed to determine the ingredients of the received fluorescence, as is described in more detail below in connection with FIG. 2.

Figure 2:
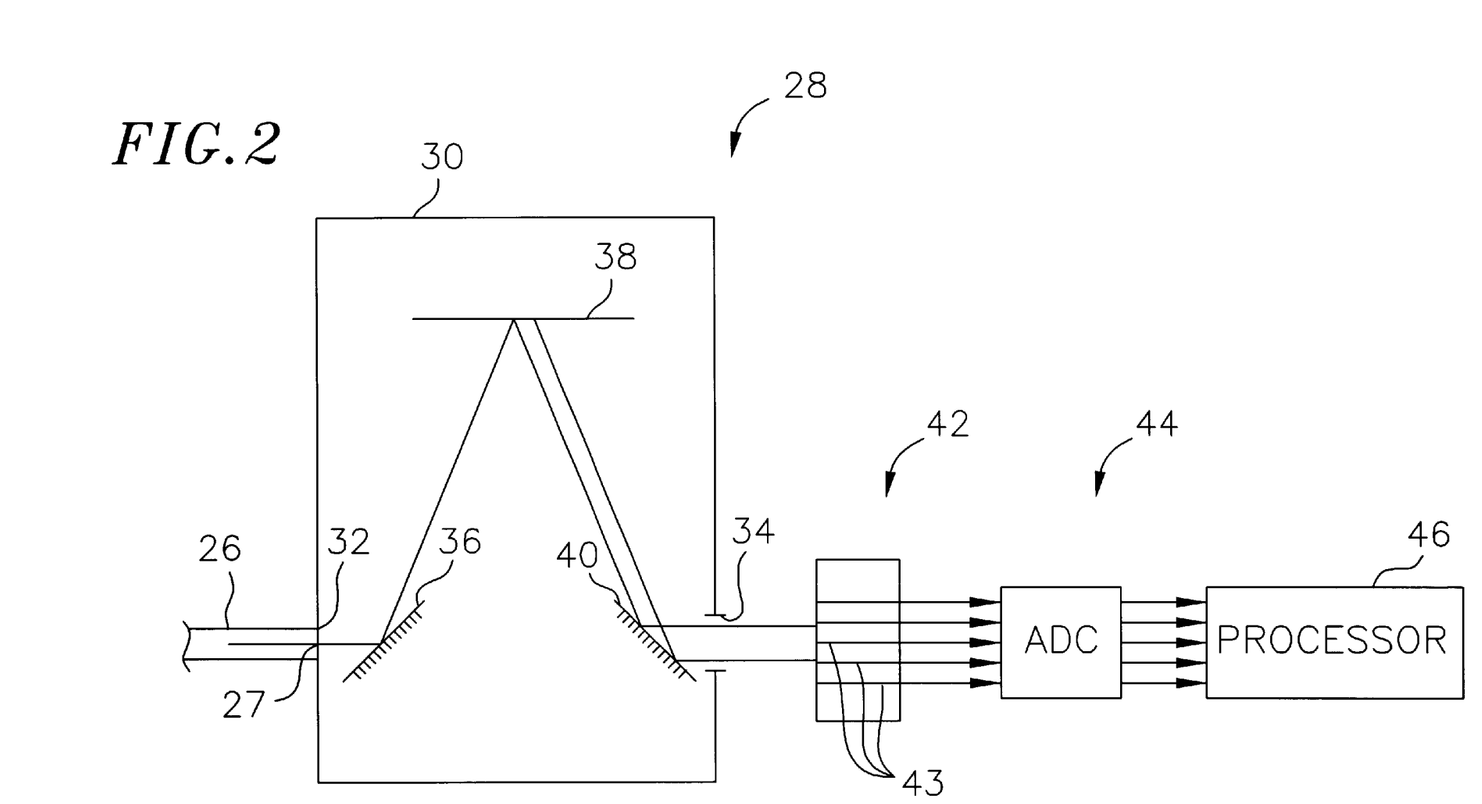
FIG. 2 is a schematic diagram that illustrates one embodiment of a spectral analyzer included in the system of FIG. 1.

Referring to FIG. 2, there is shown one illustrative embodiment of spectral analyzer 28. Spectral analyzer 28 includes a housing 30 formed with a light entrance opening 32 and a light exit opening 34. Light entrance opening 32 is connected to light guide 26 to receive light from the light guide. Preferably, the distal end of light guide 26 includes an exit slit 27 to permit the delivery of fluorescence from light guide 26 to spectral analyzer 28. Mounted within spectral analyzer 28 is a first mirror 36 that directs the incoming light to a grating 38, which disperses the light over appropriate wavelength range. The dispersed light is then directed to a second mirror 40 that directs the dispersed light through the exit opening 34. In place of the grating 38, spectral analyzer 28 may alternatively include a prism or other light-dispersing structure.

Aligned with exit opening 34 is a detector array 42 consisting of individual detectors 43. The detector array 42 may take many different forms, such as an array of photomultiplier tubes (PMTs), multiple window PMTs, position-dependant wire detectors, position/time-sensitive detectors, a photodiode array, an intensified photodiode array, charge-coupled devices (CCDs), intensified CCDs, an SIT or other video camera, or any other suitable optical-to-electrical transducer.

In any event, the detector array 42 is preferably a linear array, with the respective wavelength bands being incident upon a corresponding one of the detectors 43. Each detector 43 in the array receives the light incident upon it and generates a corresponding analog electrical signal. The electrical signals are then introduced to respective analog-to-digital converters (shown schematically at 44) which convert the incoming analog signals into corresponding digital signals. The digital signals are then delivered to a processor 46 that processes the digital signals to determine the constituents of the emissions spectra, as is described in more detail below.

Figure 3:
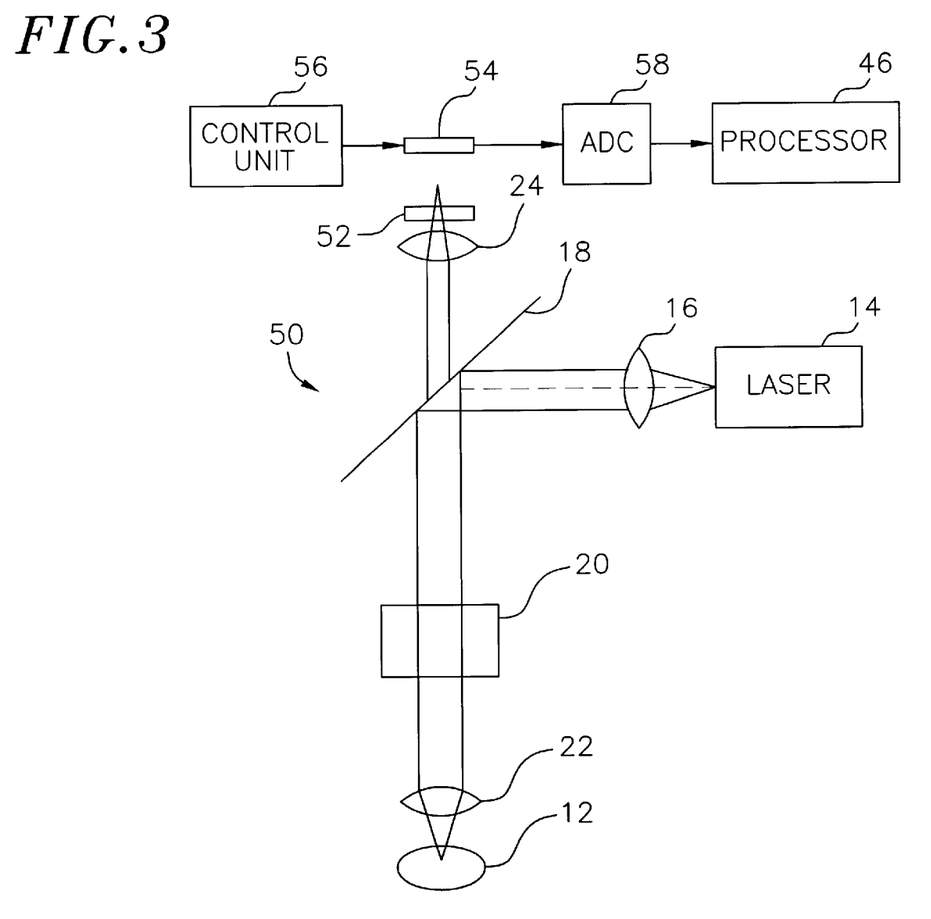
FIG. 3 is a schematic diagram that illustrates a system according to another illustrative embodiment of the invention.

Referring now to FIG. 3, there is shown a system 50 according to an alternative embodiment of the invention. In place of spectral analyzer 28, system 50 includes a tunable filter 52 that is interposed between lens 24 and a single detector 54, for example, a PMT. In one embodiment, tunable filter comprises a liquid crystal tunable filter (LCTF) that utilizes liquid crystals to continuously vary the retardance of individual filter stages, resulting in a narrow band filter that is electrically tunable over a wide spectral range. Alternatively, the tunable filter 52 may comprise an acoustooptical tunable filter. In any event, tunable filter is controlled by a suitable control unit 56 to vary the bandpass of the filter through the spectral range. At each bandpass, detector 54 receives fluorescence and generates a corresponding electrical output signal, which is converted to digital format by an analog-to-digital converter 58 and then introduced to processor 46 for processing.

Figure 4:
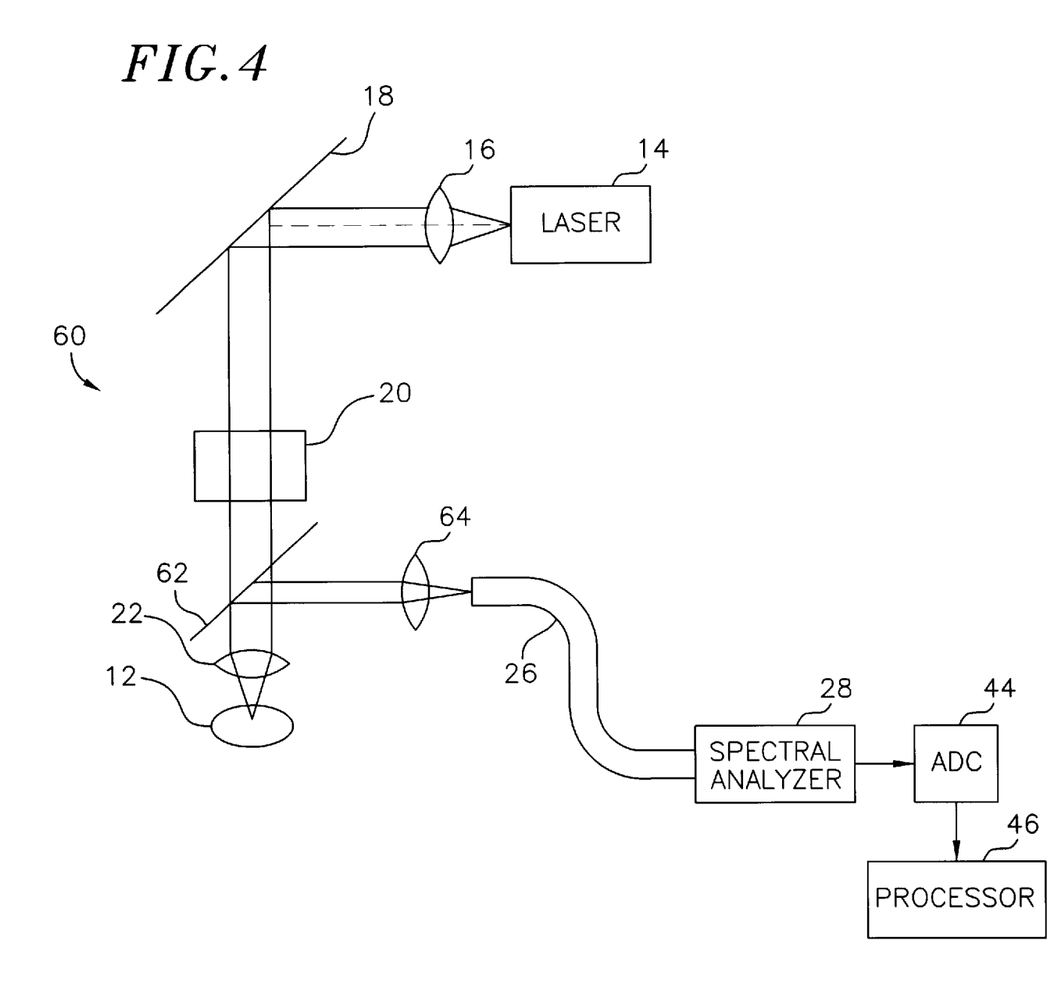
FIG. 4 is a schematic diagram that illustrates yet another illustrative embodiment of the invention.

Referring now to FIG. 4, there is shown a system 60 according to still another embodiment of the invention. System 60 includes a long pass dichroic mirror 62 placed in the light stream between the scanning optics 20 and the microscope lens 22. The dichroic mirror 62 is selected such that wavelengths corresponding to the fluorescence radiated by the specimen are reflected by the mirror 62, while the laser light from laser 14 passes through without being reflected. The reflected fluorescence is directed to a focusing lens 64, and then introduced to light guide 26 which delivers the light to spectral analyzer 28. As described above, spectral analyzer disperses the light and passes the light on to ADC 44, which converts the respective bands into digital signals and introduces the digital signals to processor 46.

System 60 is therefore suitable for use in connection with a non-descanned two-photon microscope. By diverting the radiated fluorescence before it passes through the scanning optics 20, a signal of increased intensity is received by spectral analyzer 28, as compared with a signal that passes through scanning optics 20 and dichroic mirror 18 before being received by a spectral analyzer or detector. Thus, the dwell time at each pixel can be reduced as a result.

Figure 5:
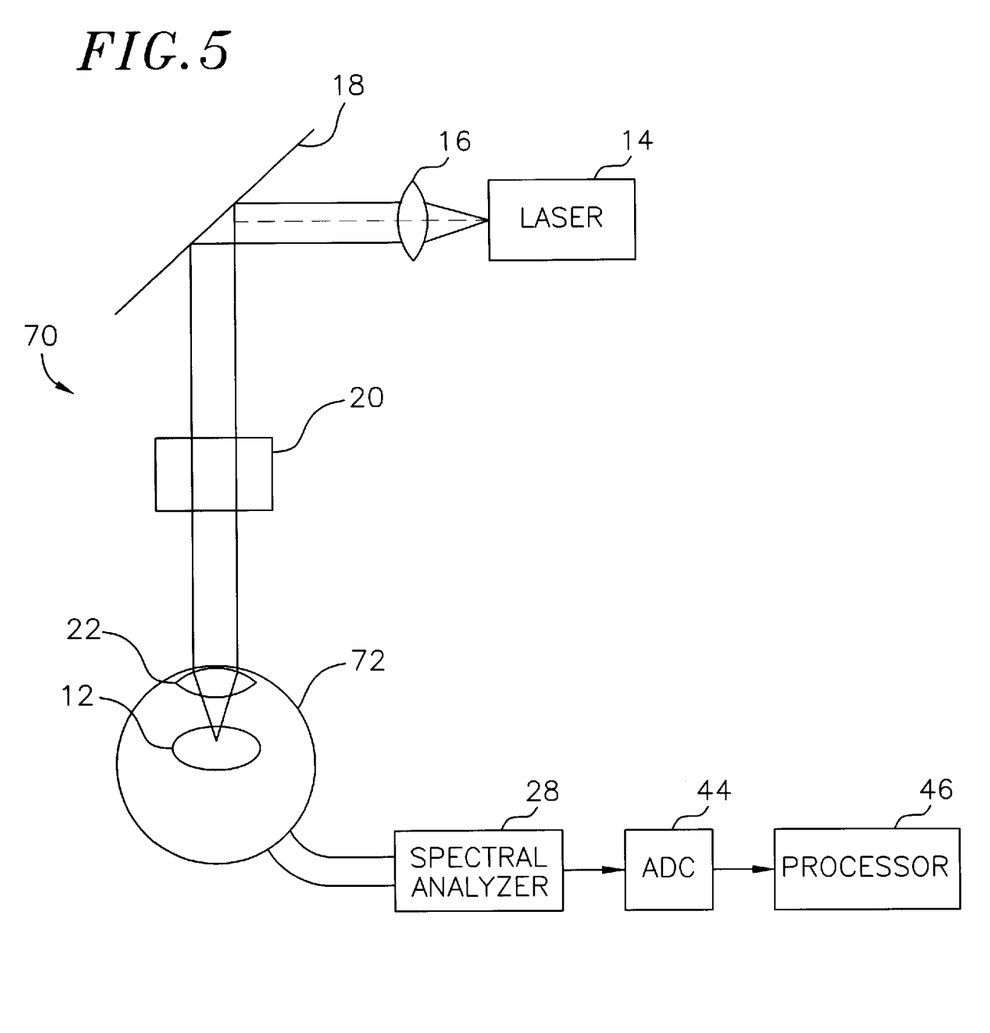
FIG. 5 is a schematic diagram that illustrates still another embodiment of the invention.

Referring now to FIG. 5, a system 70 is shown according to another embodiment of the invention. System 70 includes a light collector 72 that substantially surrounds specimen 12 and includes a reflective inner surface. Thus, light emitted by fluorescent dyes within specimen 12 are collected by the collector, regardless of the direction in which the light radiates. In one embodiment, collector 72 comprises an integrating sphere. Alternatively, collector 72 may be in the shape of an ellipsoid or other structure that substantially encompasses specimen 12 to collect a substantial amount of the light radiating from specimen 12, for example, an elliptical mirror. Collector 72 connects to light guide 26 to deliver the collected light to spectral analyzer 28.

Thus, in use of the various systems described above, laser light is directed by dichroic mirror 18, scanning optics 20, and focusing lens 22 to a region of specimen 12. The photons (either from a single-photon laser or from a multi-photon laser) excite the fluorescent dyes in the region, causing them to fluoresce. The entire emitted spectrum is received and processed simultaneously in certain of the illustrative embodiments to speed up the collection process. The spectral information is then processed to determine the amounts of each dye contributing to the emitted spectrum.

Figure 6:
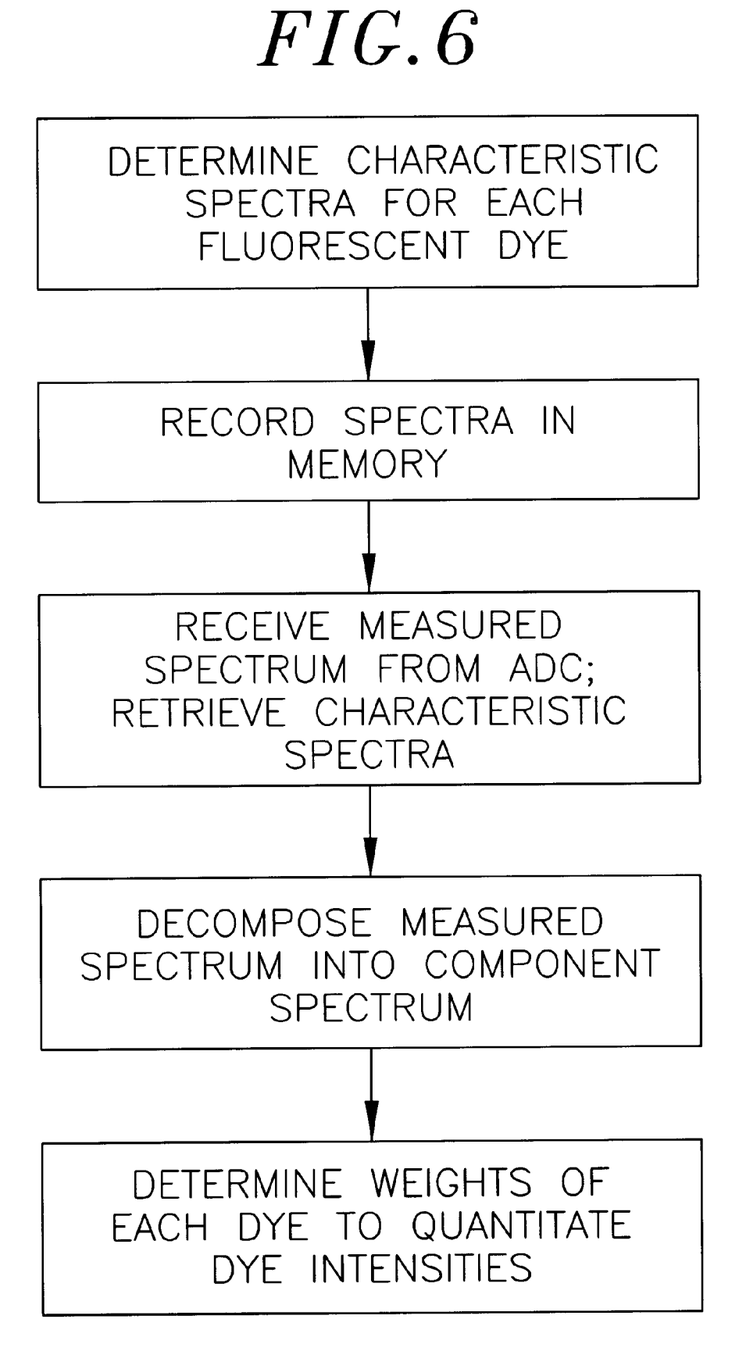
FIG. 6 is a flow chart that depicts the operational flow of processing software to process spectral data received by the systems of any of FIGS. 1 through 5 according to one illustrative embodiment of the invention.
Figure 7A:
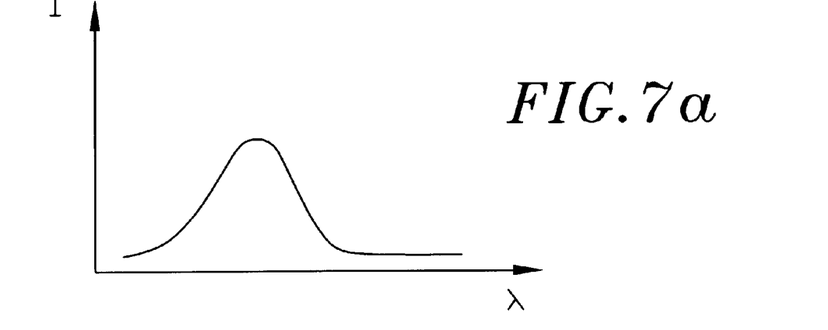
FIGS. 7a–c depict emissions spectra for various fluorescent dyes.
Figure 7B:
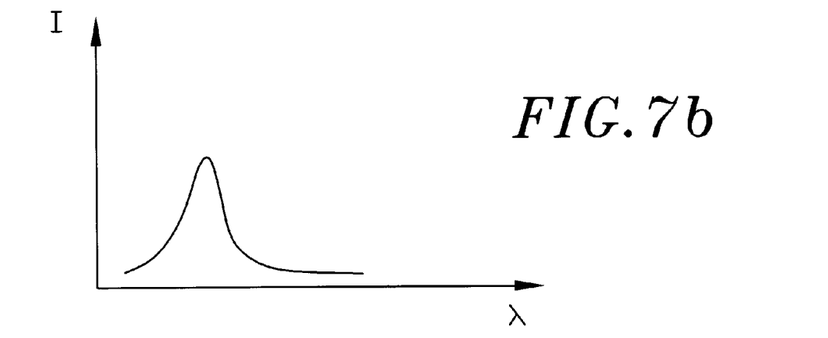
Figure 7C:
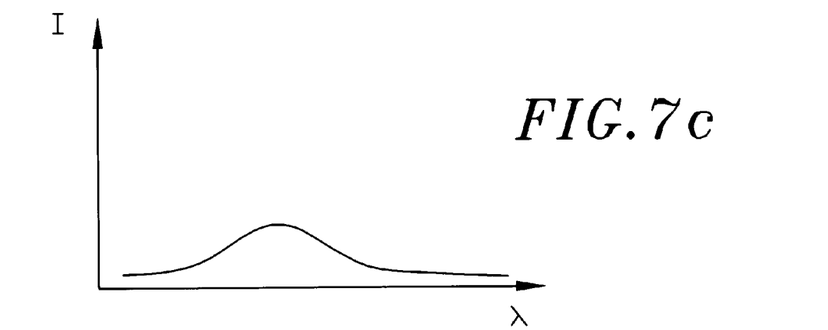

Referring now to FIG. 6, operation of processor 46 is described in greater detail. In one embodiment, processor 46 is programmed to execute a linear unmixing operation upon the incoming spectral data to approximate the quantities of each fluorescent dye that contributed to the emitted spectrum. As shown in FIG. 6, operation begins at step 100 by determining spectral characteristics for the respective individual fluorescent dyes. As is well known in the art, each of the fluorescent dyes emits a particular spectrum over a certain wavelength band and at certain varying intensities within that band (see FIGS. 7a–c which illustrate examples of emissions spectra for three different fluorescent dyes). At step 102, data relating to the probe spectra is recorded in processor memory for subsequent retrieval.

Figure 7D:
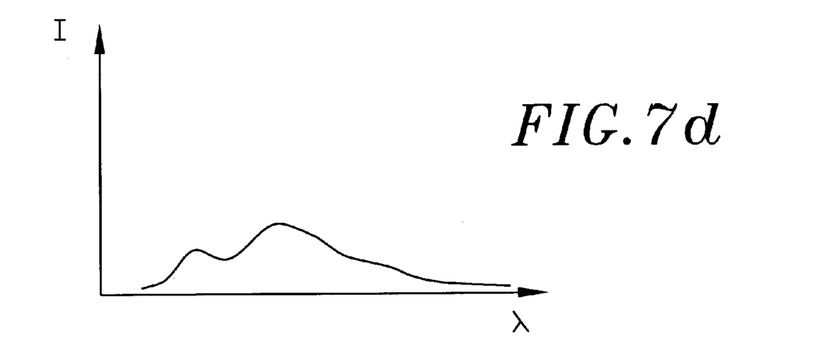
FIG. 7d depicts a measured spectrum from a specimen that contains plural different dyes.

At step 104, processor 46 receives the measured imaging spectrum data from ADC 44 (see FIG. 7d), and retrieves the characteristic spectra for the various fluorescent dyes. At step 106, the measured spectrum is decomposed into the various component dye spectra. This can be accomplished in many different ways. In one embodiment, processor 46 generates a model spectrum from the individual templates, and compares the model spectrum with the actual recorded spectrum. The respective weights of each of the individual templates are then varied to arrive at a close approximation of the actual spectrum. Then, at step 108, processor 46 determines the weights of each dye to quantitate the respective dye intensities.

In another embodiment, processor 46 is programmed to carry out principal component analysis (PCA) on the incoming data. As is well known in the art, PCA is a linear model which transforms the original variables of an emission spectrum into a set of linear combinations of the original variables called principal components, that account for the variance in the original data set. Suitable forms of PCA algorithms are disclosed in U.S. Pat. No. 5,991,653 to Richards-Kortum et al., and U.S. Pat. No. 5,887,074 to Lai et al., the disclosures of which are hereby expressly incorporated by reference.

Preferably, system 20 uses a single excitation to excite the respective dyes (i.e., the dyes are pan-excited). In this manner, all of the dyes are excited at once by using a single wavelength. Thus, there is no need for using more than one wavelength, nor is there a need to take multiple images and overlay the respective pixel images to generate a complete image. Alternatively, system 20 may use multiple excitations, such as two excitations, to excite the dyes, especially in situations where it is desirable to cover a relatively broad span of dyes.

From the foregoing, it will be apparent to those skilled in the art that the present invention provides an efficient and reliable system for receiving and processing emissions spectra in connection with fluorescence microscopy. The system processes the emissions spectra to determine concentrations of plural fluorescent dyes in a particular spectrum, even where the wavelength bands of the dyes overlap.

While the above description contains many specific features of the invention, these should not be construed as limitations on the scope of the invention, but rather as one exemplary embodiment thereof. Many other variations are possible. Accordingly, the scope of the invention should be determined not by the embodiments illustrated, but by the appended claims and their legal equivalents.

What is claimed is:

1. A method of monitoring cellular activity in a cellular specimen, comprising:

applying a plurality of different excitable markers to the specimen;

applying light to the specimen from a multi-photon laser microscope to excite a region of the specimen and cause fluorescence to be radiated from the region by the markers in that region;

separating the fluorescence into wavelength bands using a spectral analyzer; and detecting the fluorescence through an array of detectors, with each detector receiving one of the wavelength bands and generating a corresponding signal.

2. The method of claim 1, wherein separating the fluorescence includes using a grating.

3. The method of claim 1, wherein separating the fluorescence includes using a prism.

4. The method of claim 1, wherein separating the fluorescence includes using a liquid crystal tunable filter.

5. The method of claim 1, wherein separating the fluorescence includes using an acousto-optical tunable filter.

6. The method of claim 1, wherein applying a plurality of excitable markers includes applying a plurality of fluorescent probes to the specimen.

7. The method of claim 1, wherein detecting the fluorescence includes using a plurality of photomultiplier tubes.

8. The method of claim 1, wherein detecting the fluorescence includes using a plurality of high gain photomultiplier tubes.

9. The method of claim 1, wherein applying light to the specimen comprises applying light from a two-photon laser microscope.

10. A system for monitoring cellular activity in a cellular specimen that contains a plurality of excitable markers, the system comprising:
- a laser microscope that is operative to excite the markers in a region of the specimen, wherein the markers in the region radiate fluorescence as a result;
- a tunable filter that is operative to process the fluorescence and to pass a portion of the fluorescence, wherein the portion of the fluorescence is within a wavelength band that depends on the setting of the filter; and
- a detector that is operative to receive the processed fluorescence and to convert the fluorescence into a corresponding signal.

11. The system of claim 10, wherein the tunable filter comprises a liquid crystal tunable filter.

12. The system of claim 10, wherein the tunable filter comprises an acousto-optical tunable filter.

13. The system of claim 10, wherein the detector comprises a photomultiplier tube.

14. The system of claim 10, wherein the detector comprises a high-gain photomultiplier tube.

15. The system of claim 10, wherein the laser microscope comprises a multi-photon laser microscope.

16. A system for monitoring cellular activity in a cellular specimen that contains a plurality of excitable markers, the system comprising:
- a multi-photon laser microscope that is operative to excite the markers in a region of the specimen, wherein the markers in the region radiate fluorescence as a result;
- a deflector positioned relative to the specimen to deflect non-descanned fluorescence radiated by the markers;
- a spectral analyzer operative to receive the deflected, non-descanned fluorescence from the deflector and to disperse the fluorescence; and
- a detector array that is operative to receive the dispersed fluorescence from the spectral analyzer and to generate corresponding signals.

17. The system of claim 16, wherein the detector array comprises a plurality of photomultiplier tubes.

18. The system of claim 16, wherein the detector array comprises a plurality of high-gain photomultiplier tubes.

19. A method of monitoring cellular activity in a cellular specimen, comprising:
- applying a plurality of different excitable markers to the specimen;
- focusing light upon a region of the specimen from a laser microscope to excite the markers in the region and cause fluorescence to be radiated by the markers in the region;
- separating the fluorescence into wavelength bands;
- detecting the fluorescence through an array of detectors, with each detector receiving one of the wavelength bands and generating a corresponding signal; and
- processing the signals from the detectors to calculate the quantities of each marker in the region.

20. The method of claim 19, wherein separating the fluorescence includes using a grating.

21. The method of claim 19, wherein separating the fluorescence includes using a prism.

22. The method of claim 19, wherein separating the fluorescence includes using a liquid crystal tunable filter.

23. The method of claim 19, wherein separating the fluorescence includes using an acousto-optical tunable filter.

24. The method of claim 19, wherein applying a plurality of excitable markers includes applying a plurality of fluorescent probes to the specimen.

25. The method of claim 19, wherein collecting the fluorescence includes using a plurality of photomultiplier tubes.

26. The method of claim 19, wherein collecting the fluorescence includes using a plurality of high gain photomultiplier tubes.

27. The method of claim 19, wherein applying light to the specimen comprises applying light from a two-photon laser microscope.

28. The method of claim 19, wherein processing the signals comprises performing linear unmixing on the signals.

29. A system for monitoring cellular activity in a cellular specimen that contains a plurality of excitable markers, the system comprising:
- a laser microscope that is operative to excite the markers in a region of the specimen, wherein the markers in the region radiate fluorescence as a result;
- a collector that at least substantially envelops the specimen to receive fluorescence from the markers;
- a spectral analyzer connected to the collector to receive the fluorescence and process same to disperse the fluorescence; and
- a detector that is operative to receive the dispersed fluorescence and to convert the fluorescence into corresponding signals.

30. The system of claim 29, wherein the collector comprises an integrating sphere.

31. The system of claim 29, wherein the detector comprises an array of photomultiplier tubes.

32. The system of claim 29, wherein the detector comprises an array of high-gain photomultiplier tubes.

33. The system of claim 29, wherein the laser microscope comprises a multi-photon laser microscope.

* * * * *